United States Patent [19]
Son et al.

[11] Patent Number: 6,136,815
[45] Date of Patent: Oct. 24, 2000

[54] ANTIVIRAL 2,4-PYRIMIDINEDIONE DERIVATIVES AND PROCESS FOR THE PREPARATION THEREOF

[75] Inventors: Jong-Chan Son; Iii Young Lee; Hyun-Sook Kim, all of Daejeon; Jin-Chel Kim, Kyounggi-do; Eui-Hwan Cho; Sun-Gan Chung, both of Seoul; Joung-Young Kim, Kyounggi-do; Soon-Hwan Lee, Kyounggi-do; Ho-Seok Kwon, Kyounggi-do; Jae-Weung Lee, Kyounggi-do, all of Rep. of Korea

[73] Assignees: Korea Research Inst. of Chem. Tech.; Samjin Pharmaceutical Co., Ltd., both of Rep. of Korea

[21] Appl. No.: 09/180,490
[22] PCT Filed: May 15, 1997
[86] PCT No.: PCT/KR97/00084
§ 371 Date: Nov. 10, 1998
§ 102(e) Date: Nov. 10, 1998
[87] PCT Pub. No.: WO97/43266
PCT Pub. Date: Nov. 20, 1997

[30] Foreign Application Priority Data

May 16, 1996 [KR] Rep. of Korea ............ 96 16413
Apr. 14, 1997 [KR] Rep. of Korea ............ 97 13560

[51] Int. Cl.$^7$ ............ A61K 31/513; C07D 239/54
[52] U.S. Cl. ............ 514/274; 544/314
[58] Field of Search ............ 544/314; 514/274

[56] References Cited

U.S. PATENT DOCUMENTS 5,112,835  5/1992  Miyasaka et al. ............ 544/309

*Primary Examiner*—Richard L. Raymond
*Assistant Examiner*—Venkataraman Balasubramanian
*Attorney, Agent, or Firm*—Anderson Kill & Olick, PC

[57] ABSTRACT

6-aryloxy and 6-arylcarbonyl 2,4-pyrimidinedione derivatives of the formula(I) having high antiviral activity against HIV-1 and low toxicity are useful for treating AIDS:

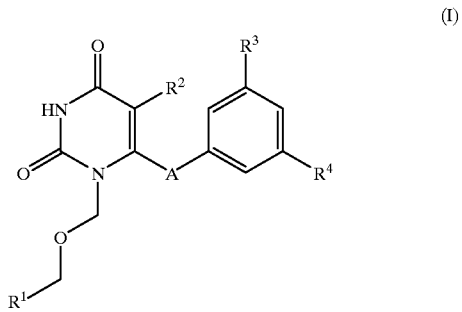

(I)

wherein:

$R^1$ is hydrogen or a $C_{1-10}$ alkyl group optionally having a substituent selected from the group consisting of aryl, hydroxy, $C_{1-10}$ alkoxy and $C_{2-5}$ alkylcarbonyloxy groups;

$R^2$ is hydrogen or a $C_{1-10}$ alkyl group optionally having an aryl substituent;

$R^3$ and $R^4$ are each hydrogen or a $C_{1-3}$ alkyl group; and

A is oxygen or a carbonyl group.

8 Claims, No Drawings

ANTIVIRAL 2,4-PYRIMIDINEDIONE DERIVATIVES AND PROCESS FOR THE PREPARATION THEREOF

FIELD OF THE INVENTION

The present invention relates to novel pyrimidinedione derivatives having 6-aryloxy or 6-arylcarbonyl substituents, which are useful as an antiviral agent, particularly for treating acquired immunodeficiency syndrome (AIDS), and pharmaceutically acceptable salts thereof. The present invention also relates to a process for the preparation of such derivatives and to a pharmaceutical composition containing same as an active ingredient.

DESCRIPTION OF THE PRIOR ART

Various compounds such as AZT (3'-azido-3'-deoxythymidine), DDC (2',3'-dideoxycytidine), DDI (2',3'-dideoxyinosine), D4T (3'-deoxy-2',3'-didehydrothymidine) 3TC(lamivudine), Nevirapine, Indinavir, Ritonavir and Saquinavir have been reported to have the ability, albeit limited, to inhibit the reproduction of AIDS virus. However, they are also known to cause undesirable side effects due to their toxicity as well as to induce the mutation of the virus, thereby increasing the resistance of the virus.

In order to minimize such problems, therefore, many attempts have been made. For example, 2,4-pyrimidinedione derivatives substituted with an alkoxymethyl group on the N-1 position thereof have been reported in *J. Med. Chem.*, 35, 4713 (1992); *J. Med. Chem.*, 35, 337 (1992); *J. Med. Chem.*, 34, 1508 (1991); *J. Med. Chem.*, 34, 1394 (1991); *J. Med. Chem.*, 34, 349 (1991); *Molecular Pharm.*, 39, 805 (1991); *Tet. Lett.*, 35, 4531 (1994); *J. Med. Chem.*, 38, 2860 (1995); *Nucleosides and Nucleotides*, 14, 575 (1995); *J. Med. Chem.*, 39, 2427 (1996); EP 0,449,726 A1; EP 0,420,763 A2; U.S. Pat. No. 5,318,972; and WO95/18109 A1 to have improved activity against human immunodeficiency virus (HIV), while exhibiting lower toxicity. However, needs have continued to exist for compounds having higher potency against HIV while exhibiting a much lower toxicity.

SUMMARY OF THE INVENTION

Accordingly, it is a primary object of the present invention to provide a novel compound having both superior antiviral activity against HIV and reduced toxicity.

It is another object of the present invention to provide a pharmaceutical composition containing same.

It is a further object of the present invention to provide a process for the preparation of said novel compound.

In accordance with one aspect of the present invention, there are provided a novel 2,4-pyrimidinedione compound of formula(I) and pharmaceutically acceptable salts thereof:

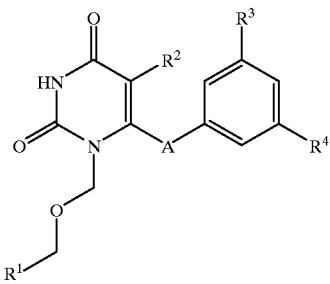

wherein:

$R^1$ is hydrogen or a $C_{1-10}$ alkyl group optionally having a substituent selected from the group consisting of aryl, hydroxy, $C_{1-10}$ alkoxy and $C_{2-5}$ alkylcarbonyloxy groups;

$R^2$ is hydrogen or a $C_{1-10}$ alkyl group optionally having an aryl substituent;

$R^3$ and $R^4$ are each hydrogen or a $C_{1-3}$ alkyl group; and

A is oxygen or a carbonyl group.

DETAILED DESCRIPTION OF THE INVENTION

Among the compounds of formula(I) of the present invention, the preferred are those wherein $R^1$ is methyl, hydroxymethyl, acetoxymethyl or phenyl.

Among the preferred compounds of the present invention, the more preferred are those wherein $R^2$ is ethyl or isopropyl.

Among the more preferred compounds of the present invention, the most preferred are those wherein $R^3$ and $R^4$ are each hydrogen or methyl.

The 2,4-pyrimidinedione compound of formula(I) may be prepared by silylating a compound of formula(II) to give a compound of formula(III) and coupling the compound of formula(III) with a compound of formula(IV), as shown in the following Reaction Scheme A:

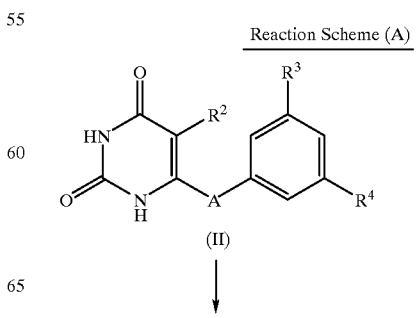

Reaction Scheme (A)

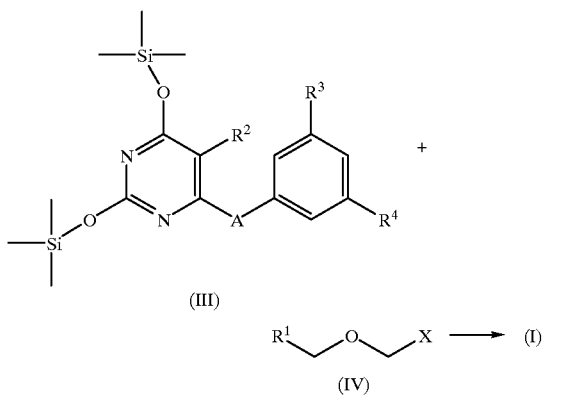

(III)

$R^1\diagdown O\diagdown X$ → (I)

(IV)

wherein:

$R^1$, $R^2$, $R^3$, $R^4$ and A have the same meanings as defined in formula(I) above; and X is halogen or acetoxy.

In Reaction Scheme A, the silylation of the compound of formula(II) may be conducted under a conventional silylation condition. Preferably, it may be carried out by refluxing the compound and 1,1,1,3,3,3-hexamethyldisilazane, which is used as a solvent and as a silylating agent, for 2 to 24 hours in the presence of a catalyst, e.g., chlorotrimethylsilane.

The reaction between the compound of formula(III) and the compound of formula(IV) may be conducted in the absence or presence of a Lewis acid at a temperature ranging from −20 to 100° C. Preferably, it may be carried out by stirring the reaction mixture at a temperature ranging from 0° C. to room temperature. For example, a mixture of the compound of formula(III) and the compound of formula(IV) in a molar ratio of 1:0.5 to 1:2, preferably, 1:0.8 to 1:1.2 may be stirred in the presence of tin tetrachloride under a nitrogen blanket at room temperature for 1 to 24 hours. Suitable for use in this reaction is a nonpolar solvent, e.g., acetonitrile, dichloromethane or 1,2-dichloroethane.

The compound of formula(II) may be prepared in accordance with the procedure disclosed in PCT International Publication WO95/18109, as illustrated in Reaction Scheme B below.

Reaction Scheme (B)

Method (i): A is C=O

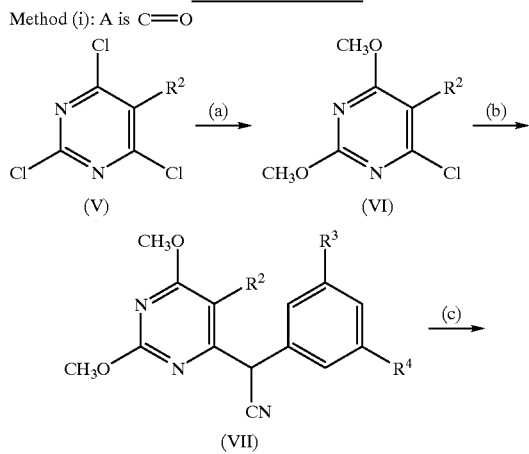

Method (ii): A is O

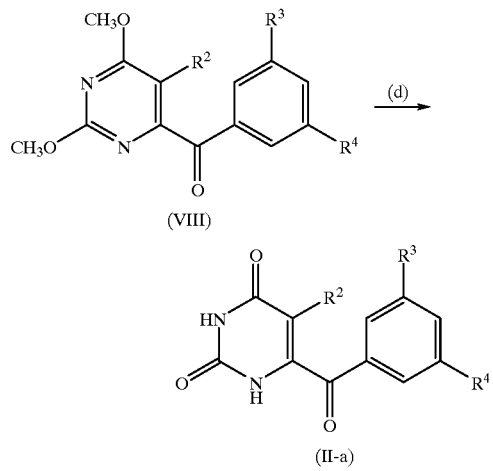

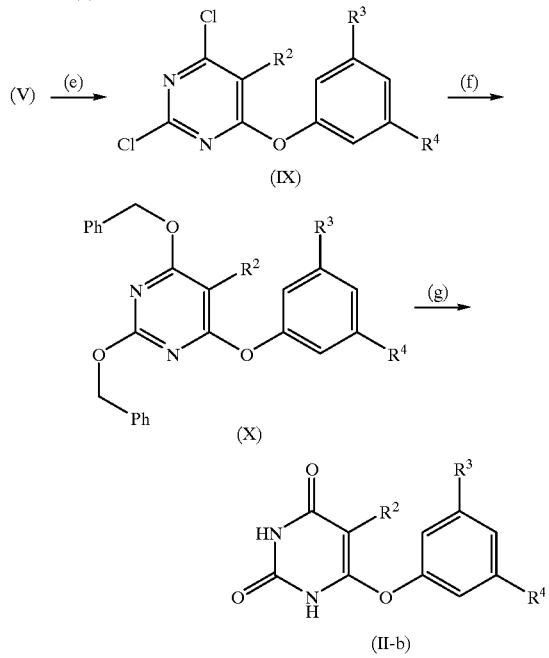

wherein, $R^2$, $R^3$ and $R^4$ have the same meanings as defined previously in conjunction with formula(I).

In accordance with the method (i) in Reaction Scheme B, a compound of formula (V) is methoxylated using a known method disclosed in, e.g., *Ber.*, 52B, 869 (1919) and *J. Med. Chem.*, 7, 808 (1964) to provide a compound of formula (VI) (Step (a)). Preferably, Step (a) may be carried out by reacting the compound of formula(V) with sodium methoxide at room temperature. The compound of formula(VI) is then subjected to a coupling reaction with an acetonitrile derivative in a polar solvent, e.g., dimethylformamide, in the presence of a strong base, e.g., sodium hydroxide, to provide a compound of formula(VII)(Step (b)). The compound of formula(VII) is reacted with a base, e.g., sodium hydride, in a polar solvent, e.g., dimethylformamide, to give a compound of formula(VIII) (Step (c)). Then, the compound of formula(VIII) may be hydrolyzed with an acid, e.g., hydrochloric acid, to provide a compound of formula (II-a).

In the method (ii) of Reaction Scheme B, the compound of formula (V) is reacted with a phenol derivative in the presence of a base, e.g., sodium hydride, in a polar solvent, e.g., dimethylformamide, to provide a compound of formula (IX) (Step (e)). The compound of formula(IX) is treated with an alkali metal, e.g., sodium, and then reacted with benzyl alcohol to provide a compound of formula (X) (Step (f)). Then, the compound of formula(X) is hydrogenated in the presence of a palladium catalyst in an alcohol solvent, e.g., ethanol, to provide a compound of formula(II-b) (Step (g)).

Exemplary compounds of formula(I) of the present invention which can be prepared in accordance with the methods described above are listed below:

1
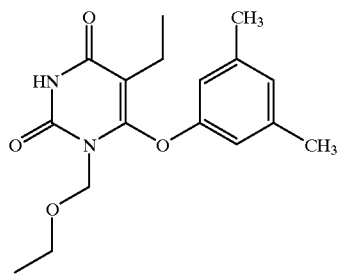

2
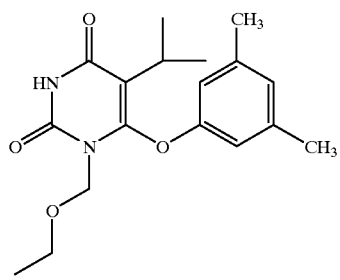

3
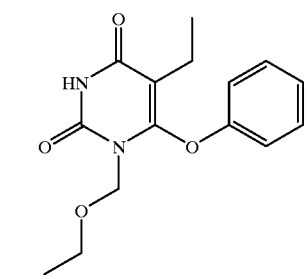

4
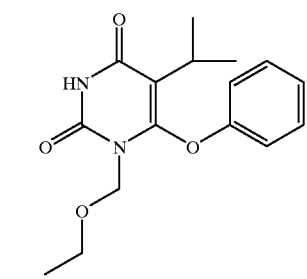

5
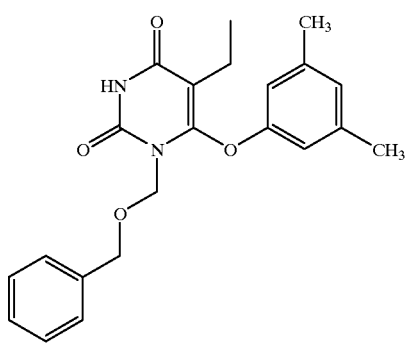

6
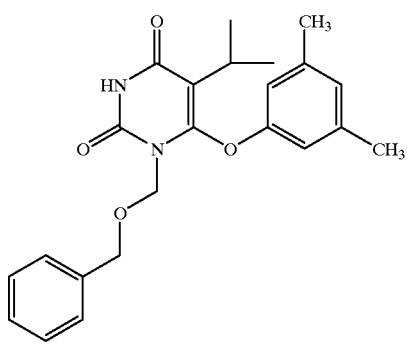

7
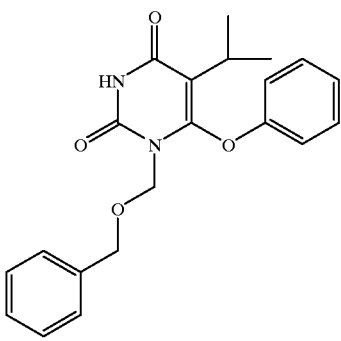

8
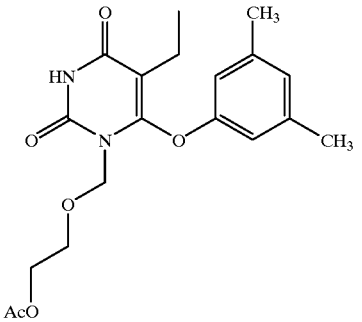

9
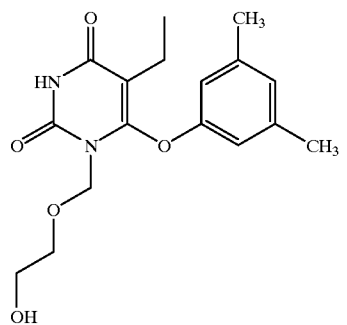
10
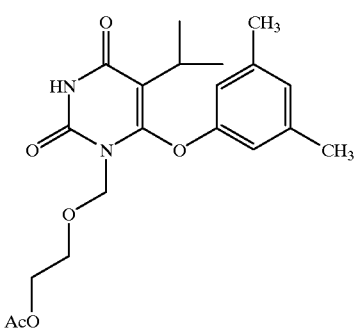
11
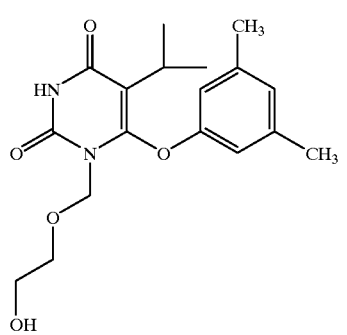
12
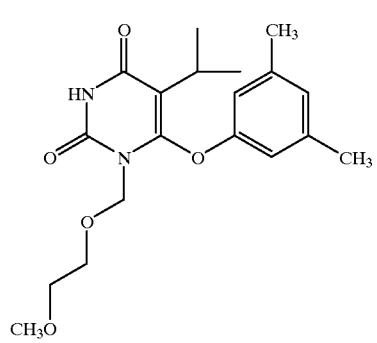
13
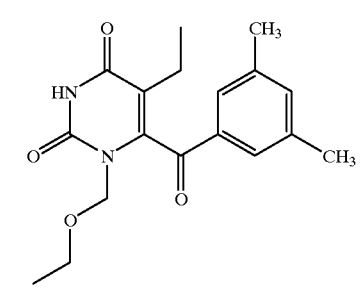
14
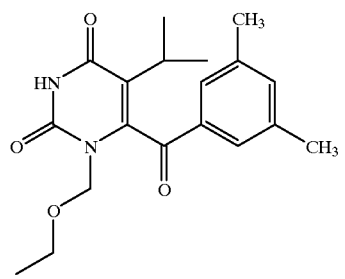
15
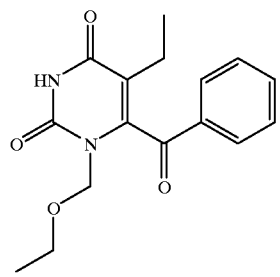
16
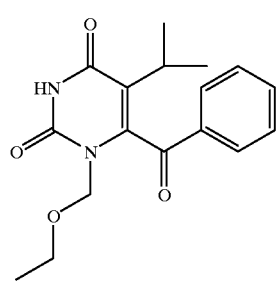
17
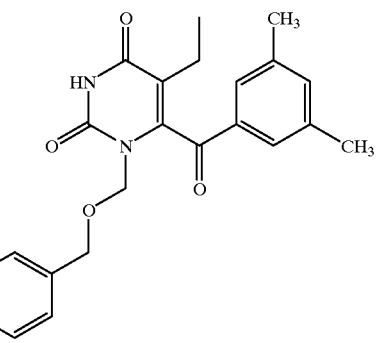
18
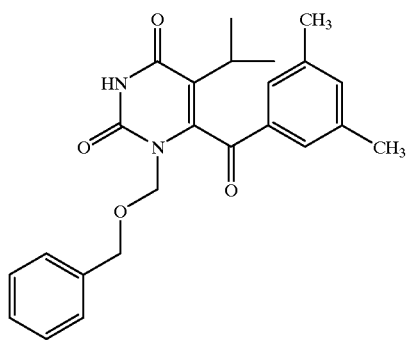

-continued

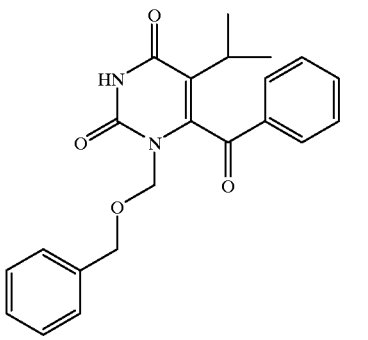

19

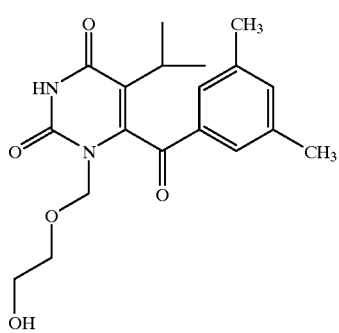

20

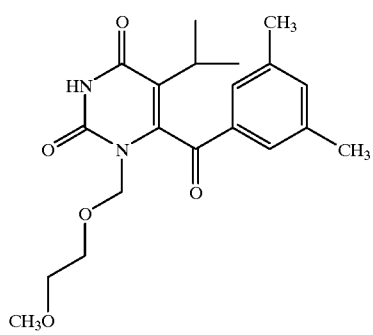

21

Furthermore, the present invention encompasses, within its scope, those pharmaceutically acceptable salts of the compounds of formula(I). Suitable pharmaceutically acceptable salts of the 2,4-pyrimidinedione compounds(I) possessing strong antiviral activity against HIV may include alkali or alkaline earth metal salts, e.g., sodium, potassium, magnesium and calcium salts thereof.

The present invention also includes within its scope pharmaceutical compositions comprising one or more of the compounds of formula(I) and their above-mentioned salts as the active ingredient, in association with pharmaceutically acceptable carriers, excipients or other additives, if necessary.

The pharmaceutical compositions of the invention may be formulated for administration orally or by injection. The composition for oral administration may take various forms such as tablets and gelatin capsules, which may contain conventional additives such as a diluent (e.g., lactose, dextrose, sucrose, mannitol, sorbitol, cellulose and/or glycine), a lubricant (e.g., silica, talc, stearic acid or its magnesium and calcium salts and polyethylene glycol). In the case of the tablet form, the composition may further comprise a binder (e.g., magnesium aluminum silicate, starch paste, gelatin, tragacanth, methyl cellulose, sodium carboxymethyl cellulose and polyvinyl picolidine) and optionally a disintegrant (e.g., starch, agar and alginic acid or its sodium salt), absorbent, colorant, flavor, sweetener and the like. The composition for injection may be an isotonic solution or a suspension.

The composition may be sterilized and/or contain an adjuvant such as a preservative, stabilizer, wetting agent, emulsifier, a salt for controlling an osmotic pressure and/or a buffer solution, and other pharmaceutically effective materials.

The pharmaceutical compositions can be prepared by a conventional mixing, granulating or coating method and may contain preferably about 0.1 to 75%, more preferably about 1 to 50% of the active ingredient of this invention. The unit dosage of the composition suitable for administering a person weighing about 50 to 70 kg may contain about 10 to 200 mg of the active ingredient.

The following Preparation and Examples are given for the purpose of illustration only and are not intended to limit the scope of the invention.

In the Preparation and Examples, unless otherwise specified, the evaporation was conducted under a reduced pressure, preferably under a pressure ranging from about 15 to 100 mmHg.

Preparation

The compounds of formula(II) having one of the structures (A) to (H) shown below may be used in preparing the compound of formula(I) of the present invention. The compounds having the specified structures (A) to (H) were prepared in accordance with the procedures described in PCT Publication WO95/18109.

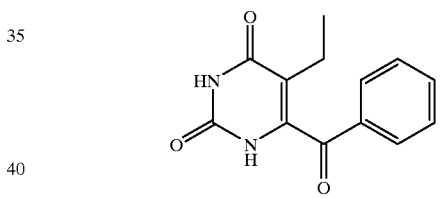

(A)

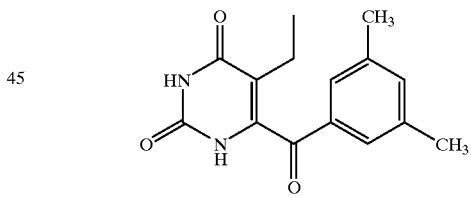

(B)

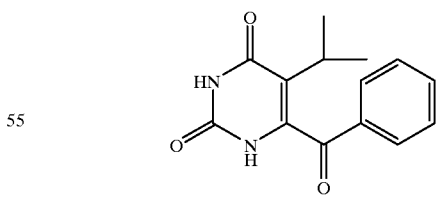

(C)

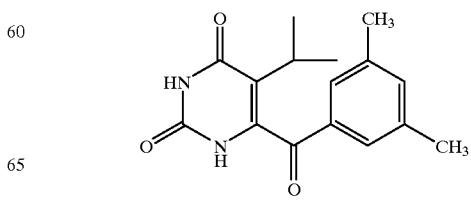

(D)

-continued

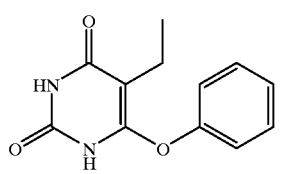

(E)

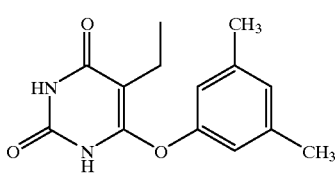

(F)

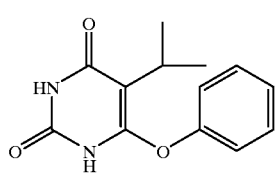

(G)

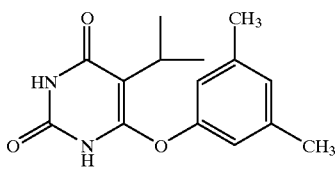

(H)

The melting points and NMR data of the compounds of structural formulae (A) to (H) obtained as above are summarized in Table 1 below.

TABLE 1

| Compound | Melting Point (° C.) | $^1$H-NMR |
|---|---|---|
| A | 218–219 | (200MHz, CD$_3$OD) δ 0.98 (3H, t, J=7.5Hz), 2.17 (2H, q, J=7.5Hz), 7.58–8.03 (5H, m) |
| B | 249–250 | (200MHz, CD$_3$OD) δ 0.97 (3H, t, J=7.4Hz), 2.17 (2H, q, J=7.4Hz), 2.39 (6H, s), 7.32 (1H, s), 7.50 (2H, s) |
| C | 220–221 | (200MHz, CD$_3$OD) δ 1.16 (6H, d, J=7.0Hz), 2.45 (1H, m), 7.61–8.02 (5H, m) |
| D | 238–239 | (200MHz, CDCl$_3$/CD$_3$OD) δ 1.16 (6H, d, J=6.9Hz), 2.35–2.49 (7H, m), 7.35 (1H, s), 7.53 (2H, s) |
| E | 242–243 | (200MHz, CD$_3$OD) δ 0.95 (3H, t, J=7.5Hz), 2.25 (2H, q, J=7.5Hz), 7.05–7.45 (5H, m) |
| F | 221–222 | (200MHz, CD$_3$OD) δ 0.90 (3H, t, J=7.4Hz), 2.17–2.25 (8H, m), 6.62 (2H, s), 6.78 (1H, s) |
| G | 214–215 | (200MHz, CD$_3$OD) δ 1.16 (6H, d, J=7.0Hz), 2.98 (1H, m), 7.04–7.45 (5H, m) |
| H | 229–230 | (200MHz, CD$_3$OD) δ 1.20 (6H, d, J=7.1Hz), 2.33 (6H, s), 3.35 (1H, m), 6.64 (2H, s), 6.83 (1H, s) |

EXAMPLE 1

Synthesis of 1-ethoxymethyl-5-ethyl-6-(3',5'-dimethylphenoxy)-2,4-pyrimidinedione (Compound 1)

5 ml of 1,1,1,3,3,3-hexamethyldisilazane and 5 µl of trichlorotrimethylsilane (0.05 mmol) were added to 260 mg of the compound (F) (1 mmol) obtained in the Preparation and the mixture was refluxed at 130 to 140° C. for about 14 hours. Then, the solvent was removed under a reduced pressure and the residue was dissolved in 5 ml of acetonitrile. To the resulting solution were added 93 µl of chloromethylethylether (1 mmol) and 100 µl of 1M tin tetrachloride solution in dichloromethane (0.1 mmol), and the mixture was stirred at room temperature for about 24 hours. Then, an excess amount of anhydrous sodium bicarbonate was added thereto, followed by stirring for about 30 minutes. The solvent was removed under a reduced pressure and the residue was subjected to column chromatography using a mixture of ethylacetate and hexane (1:2) as an eluent to afford 207 mg (yield 65%) of the title compound as a white solid.

Melting Point: 139–140° C.

$^1$H-NMR (200 MHz, CDCl$_3$) δ 0.92(3H, t, J=7.5 Hz), 1.09(3H, t, J=7.0 Hz), 2.19(2H, q, J=7.5 Hz), 2.28(6H, s), 3.57(2H, q, J=7.0 Hz), 5.20(2H, s), 6.56(2H, s), 6.75(1H, s), 9.04(1H, s).

EXAMPLE 2

Synthesis of 1-ethoxymethyl-5-isopropyl-6-(3',5'-dimethylphenoxy)-2,4-pyrimidinedione (Compound 2)

The procedure of Example 1 was repeated except that the compound (H) obtained in the Preparation was used in place of the compound (F) to afford 145 mg (yield 44%) of the title compound as a white solid.

Melting Point: 134–135° C.

$^1$H-NMR (500 MHz, CDCl$_3$) δ 1.10(3H, t, J=7.0 Hz), 1.13(6H, d, J=7.0 Hz), 2.30(6H, s), 2.79(1H, m), 3.55(2H, q, J=7.0 Hz), 5.18(2H, s), 6.56(2H, s), 6.76(1H, s), 8.92(1H, s).

EXAMPLE 3

Synthesis of 1-ethoxymethyl-5-ethyl-6-phenoxy-2,4-pyrimidinedione (Compound 3)

The procedure of Example 1 was repeated except that the compound (A) obtained in the Preparation was used in place of the compound (F) to afford 86 mg (yield 30%) of the title compound as a white solid.

Melting Point: 130–131° C.

$^1$H-NMR (200 MHz, CDCl$_3$) δ 0.93(3H, t, J=7.3 Hz), 1.09(3H, t, J=7.0 Hz), 2.21(2H, q, J=7.3 Hz), 3.58(2H, q, J=7.0 Hz), 5.25(2H, s), 6.97–7.45(5H, s), 8.56(1H, s).

EXAMPLE 4

Synthesis of 1-ethoxymethyl-5-isopropyl-6-phenoxy-2,4-pyrimidinedione (Compound 4)

The procedure of Example 1 was repeated except that the compound (G) obtained in the Preparation was used in place of the compound (F) to afford 95 mg (yield 31%) of the title compound as a white solid.

Melting Point: 137–138° C.

$^1$H-NMR (200 MHz, CDCl$_3$) δ 1.04(3H, t, J=7.0 Hz), 1.13(6H, d, J=7.0 Hz), 2.78(1H, m), 3.53(2H, q, J=7.0 Hz), 5.17(2H, s), 6.94–7.39(5H, m), 8.36(1H, s).

EXAMPLE 5

Synthesis of 1-benzyloxymethyl-5-ethyl-6-(3',5'-dimethylphenoxy)-2,4-pyrimidinedione (Compound 5)

The procedure of Example 1 was repeated except that chlorobenzylether was used in place of chloromethylethylether to afford 130 mg (yield 34%) of the title compound as a white solid.

Melting Point: 146–150° C.

$^1$H-NMR (200 MHz, CDCl$_3$) δ 0.93(3H, t), 2.14(2H, q), 2.27(6H, s), 4.63(2H, s), 5.28(2H, s), 6.55(2H, s), 6.76(1H, s), 7.26(5H, s).

EXAMPLE 6

Synthesis of 1-benzyloxymethyl-5-isopropyl-6-(3',5'-dimethylphenoxy)-2,4-pyrimidinedione (Compound 6)

The procedure of Example 1 was repeated except that the compound (H) obtained in the Preparation and chloromethylbenzylether were used in place of the compound (F) and chloromethylethylether, respectively, to afford 145 mg (yield 37%) of the title compound as a white solid.

Melting Point: 150–152° C.

$^1$H-NMR (500 MHz, CDCl$_3$) δ 6 1.12(6H, d, J=7.0 Hz), 2.27(6H, s), 2.78(1H, m), 4.61(2H, s), 5.24(2H, s), 6.52(2H, s), 6.75(1H, s), 7.20(2H, d, J=7.0 Hz), 7.28–7.33(3H, m), 8.54(1H, s).

EXAMPLE 7

Synthesis of 1-benzyloxymethyl-5-isopropyl-6-phenoxy-2,4-pyrimidinedione (Compound 7)

The procedure of Example 1 was repeated except that the compound (G) obtained in the Preparation and chloromethylbenzylether were used in place of the compound (F) and chloromethylethylether, respectively, to afford 190 mg (yield 52%) of the title compound as a white solid.

Melting Point: 118° C.

$^1$H-NMR (200 MHz, CDCl$_3$) δ 1.12(6H, d, J=7.0 Hz), 2.78(1H, m), 4.60(2H, s), 5.25(2H, s), 6.92–7.37(10H, m), 8.72(1H, s).

EXAMPLE 8

Synthesis of 1-(2'-acetoxyethoxymethyl)-5-ethyl-6-(3',5'-dimethylphenoxy)-2,4-pyrimidinedione (Compound 8)

The procedure of Example 1 was repeated except that chloromethyl-2-acetoxyethylether was used in place of chloromethylethylether to afford 180 mg (yield 48%) of the title compound a colorless oil.

$^1$H-NMR (500 MHz, CDCl$_3$) δ 0.94(3H, t, 7.5Hz), 2.03 (3H, s), 2.20(2H, q, J=7.0 Hz), 2.30(6H, s), 3.80(2H, t J=4.5 Hz), 4.11(2H, t, J=4.5 Hz), 5.28(2H, s), 6.58(2H, s), 6.78 (1H, s), 9.48(1 H, s).

EXAMPLE 9

Synthesis of 1-(2'-hydroxyethoxymethyl)-5-ethyl-6-(3',5'-dimethylphenoxy)-2,4-pyrimidinedione (Compound 9)

150 mg (0.4 mmol) of the compound obtained in Example 8 (Compound 8) was dissolved in 5 ml of methanol and 3 ml of aqueous ammonia was added thereto, and stirred at room temperature for 2 hours. Then, the reaction mixture was concentrated under a reduced pressure and the residue was subjected to column chromatography using a mixture of dichloromethane and methanol (15:1) as an eluent to afford 75 mg (yield 56%) of the title compound as a white solid.

Melting Point: 92–93° C.

$^1$H-NMR (500 MHz, CDCl$_3$) δ 1.09(3H, t, J=7.5 Hz), 2.34(6H, s), 2.43(2H, q, J=7.5 Hz), 3.74(4H, q, J=7.5 Hz), 5.42(2H, s), 6.70(2H, s), 6.91(1H, s), 7.93(1H, s).

EXAMPLE 10

Synthesis of 1-(2'-acetoxyethoxymethyl)-5-isopropyl-6-(3',5'-dimethylphenoxy)-2,4-pyrimidinedione (Compound 10)

The procedure of Example 8 was repeated except that the compound (H) obtained in the Preparation was used in place of the compound (F) to afford 150 mg (yield 38%) of the title compound as a white solid.

Melting Point: 115–117° C.

$^1$H-NMR (500 MHz, CDCl$_3$) δ 1.13(6H, d, J=7.0 Hz), 2.03(3H, s), 2.30(6H, s), 2.75–2.80(1H, m), 3.76(2H, t, J=5.0 Hz), 4.09(2H, t, J=5.0 Hz), 5.22(2H, s), 6.56(2H, s), 6.77(1H, s), 8.40(1H, s).

EXAMPLE 11

Synthesis of 1-(2'-hydroxyethoxymethyl)-5-isopropyl-6-(3',5'-dimethylphenoxy)-2,4-pyrimidinedione (Compound 11)

The procedure of Example 9 was repeated except that the compound obtained in Example 10 (Compound 10) was used in place of Compound 8 to afford 110 mg (yield 32%) of the title compound as a colorless oily form.

$^1$H-NMR (500 MHz, CDCl$_3$) δ 1.14(6H, d, J=7.0 Hz), 2.31(6H, s), 2.77(1H, m), 3.62(2H, d, J=5.0 Hz), 3.64(2H, d, J=5.0 Hz), 5.24(2H, s), 6.58(2H, s), 6.78(1H, s), 8.62(1H, s).

EXAMPLE 12

Synthesis of 1-(2'-methoxyethoxymethyl)-5-isopropyl-6-(3',5'-dimethylphenoxy)-2,4-pyrimidinedione (Compound 12)

The procedure of Example 1 was repeated except that chloromethyl-2-methoxyethylether was used in place of chloromethylethylether to afford 184 mg (yield 51%) of the title compound as a white solid.

Melting Point: 80–83 °C.

$^1$H-NMR (500 MHz, CDCl$_3$) δ 1.13(6H, d, J=7.0 Hz), 2.30(6H, s), 2.78(1H, m), 3.31(3H, s), 3.41(2H, t, J=4.5 Hz), 3.72(2H, t, J=4.5 Hz), 5.23(2H, s), 6.50(2H, s), 6.76(1H, s), 8.75(1H, s).

EXAMPLE 13

Synthesis of 1-ethoxymethyl-5-ethyl-6-(3',5'-dimethylbenzoyl)-2,4-pyrimidinedione (Compound 13)

The procedure of Example 1 was repeated except that the compound (B) obtained in the Preparation was used in place of the compound (F) to afford 146 mg (yield 44%) of the title compound as a white solid.

Melting Point: 184° C.

$^1$H-NMR (200 MHz, CDCl$_3$) δ 0.82(3H, t, J=7.0 Hz), 0.93(3H, t, J=7.3 Hz), 1.97–2.37(8H, m), 3.28–3.47(2H, m), 4.93(1H, d, J=10.3 Hz), 5.40(1H, d, J=10.3 Hz), 7.29(1H, s), 7.35(2H, s), 10.19(1H, s).

EXAMPLE 14

Synthesis of 1-ethoxymethyl-5-isopropyl-6-(3',5'-dimethylbenzoyl)-2,4-pyrimidinedione (Compound 14)

The procedure of Example 1 was repeated except that the compound (D) obtained in the Preparation was used in place of the compound (F) to afford 172 mg (yield 50%) of the title compound as a white solid.

Melting Point: 120–122° C.

$^1$H-NMR (200 MHz, CDCl$_3$) δ 0.81(3H, t, J=7.0 Hz), 1.13(3H, d, J=6.8 Hz), 1.22(3H, d, J=6.8 Hz), 2.29–2.40(7H, m), 3.30–3.47(2H, m), 4.88(1H, d, J=10.3 Hz), 5.41(1H, d, J=10.3 Hz), 7.31(1H, s), 7.56(2H, s), 8.85(1H, s).

EXAMPLE 15

Synthesis of 1-ethoxymethyl-5-ethyl-6-benzoyl-2,4-pyrimidinedione (Compound 15)

The procedure of Example 1 was repeated except that the compound (A) obtained in the Preparation was used in place of the compound (F) to afford 180 mg (yield 60%) of the title compound as a white solid.

Melting Point: 133–134° C.

$^1$H-NMR (200 MHz, CDCl$_3$) δ 0.78(3H, t, J=7.0 Hz), 0.95(3H, t, J=7.3 Hz), 2.02–2.29(2H, m), 3.26–3.44(2H, m), 4.90(1H, d, J=10 Hz), 5.43(1H, d, J=10 Hz), 7.49–7.97(5H, m), 8.77(1H, s).

EXAMPLE 16

Synthesis of 1-ethoxymethyl-5-isopropyl-6-benzoyl-2,4-pyrimidinedione (Compound 16)

The procedure of Example 1 was repeated except that the compound (C) obtained in the Preparation was used in place of the compound (F) to afford 244 mg (yield 77%) of the title compound as a white solid.

Melting Point: 144–145° C.

$^1$H-NMR (200 MHz, CDCl$_3$) δ 0.74(3H, t, J=7.0 Hz), 1.12(3H, d, J=6.8 Hz), 1.21(3H, d, J=6.8 Hz), 2.33(1H, m), 3.21–3.42(2H, m), 4.83(1H, d, J=10.2 Hz), 5.43(1H, d, J=10.2 Hz), 7.49–7.97(5H, m), 8.85(1H, s).

EXAMPLE 17

Synthesis of 1-benzyloxymethyl-5-ethyl-6-(3',5'-dimethylbenzoyl)-2,4-pyrimidinedione (Compound 17)

The procedure of Example 1 was repeated except that chloromethylbenzylether was used in place of chloromethylethylether to afford 252 mg (yield 64%) of the title compound as a white solid.

Melting Point: 115–116° C.

$^1$H-NMR (200 MHz, CDCl$_3$) δ 0.96(3H, t, J=7.4 Hz), 2.06–2.29(8H, m), 4.41(1H, d, J=12.0 Hz), 4.45(1H, d, J=12.0 Hz), 5.07(1H, d, J=10.5 Hz), 5.44(1H, d, J=10.5 Hz), 6.96–7.51(8H, m), 10.32(1H, s).

EXAMPLE 18

Synthesis of 1-benzyloxymethyl-5-isopropyl-6-(3', 5'-dimethylbenzoyl)-2,4-pyrimidinedione (Compound 18)

The procedure of Example 1 was repeated except that the compound (D) obtained in the Preparation and chloromethylbenzylether were used in place of the compound (F) and chloromethylethylether, respectively, to afford 270 mg (yield 66%) of the title compound as a white solid.

Melting Point: 68–70° C.

$^1$H-NMR (200 MHz, CDCl$_3$) 1.13(3H, d, J=6.8 Hz), 1.23(3H, d, J=6.8 Hz), 2.06–2.40(7H, m), 4.40(1H, d, J=12.0 Hz), 4.46(1H, d, J=12.0 Hz), 5.01(1H, d, J=10.4 Hz), 6.94–7.53(8H, m), 8.35(1H, s).

EXAMPLE 19

Synthesis of 1-benzyloxymethyl-5-isopropyl-6-benzoyl-2,4-pyrimidinedione (Compound 19)

The procedure of Example 1 was repeated except that the compound (C) obtained in the Preparation and chloromethylbenzylether were used in place of the compound (F) and chloromethylethylether, respectively, to afford 210 mg (yield 55%) of the title compound as a white solid.

Melting Point: 184° C.

$^1$H-NMR (200 MHz, CDCl$_3$) δ 1.16(3H, d, J=6.7 Hz), 1.26(3H, d, J=6.7 Hz), 2.41(1H, m), 4.38(1H, d, J=12.1 Hz), 4.47(1H, d, J=12.1 Hz), 5.02(1H, d, J=10.6 Hz), 5.46(1H, d, J=10.6 Hz), 6.96–7.99(10H, m), 8.74(1H, s).

EXAMPLE 20

Synthesis of 1-(2'-hydroxyethoxymethyl)-5-isopropyl-6-(3',5'-dimethylphenoxy)-2,4-pyrimidinedione (Compound 20)

The procedures of Examples 8 and 9 were repeated except that the compound (D) obtained in the Preparation was used in place of the compound (F) to afford 90 mg (yield 25%) of the title compound as a white solid.

Melting Point: 145–151° C.

$^1$H-NMR (500 MHz, CDCl$_3$) δ 1.13(3H, d, J=7.0 Hz), 1.21(3H, d, J=7.0 Hz), 2.36(1H, m), 2.40(6H, s), 3.46–3.49 (3H, m), 3.55(1H, m), 5.09(1H, d, J=10.5 Hz), 5.19(1H, d, J=10.5 Hz), 7.34(1H, s), 7.57(2H, s), 8.40(1H, s).

EXAMPLE 21

Synthesis of 1-(2'-methoxyethoxymethyl)-5-isopropyl-6-(3',5'-dimethylbenzoyl)-2,4-pyrimidinedione (Compound 21)

The procedure of Example 1 was repeated except that the compound (D) obtained in the Preparation and chloromethyl-2-methoxyethylether were used in place of the compound (F) and chloromethyl-2-methoxyethylether, respectively, to afford 170 mg (yield 45%) of the title compound as a white solid.

Melting Point: 97–99° C.

$^1$H-NMR (200 MHz, CDCl$_3$) δ 1.12(3H, d, J=7.0 Hz), 1.20(3H, d, J=7.0 Hz), 2.35(1H, m), 2.40(6H, s), 3.12(1H, m), 3.20(3H, s), 3.22(1H, m), 3.49–3.56(2H, m), 4.96(1H, d, J=10.5 Hz), 5.38(1H, d, J=10.5 Hz), 7.31(1H, s), 7.56(2H, s), 8.94(1H, s).

Antiviral Activity and Toxicity Test

The in vitro anti-HIV-1 assays were based on the inhibition of the virus-induced cytopathic effect in MT-4 cells as described in *J. Med. Chem*, 34, 349 (1991).

First, MT-4 cells were suspended in a culture medium at a concentration of 1×10$^4$ cells/ml and infected with 500 TCID$_{50}$ (50% cell culture infective dose)/well of HIV-1. Immediately after the virus infection, 100 μl of the cell suspension was brought into each well of a flat-bottomed microtiter tray containing various concentrations of the test compounds(1) to (21). After incubating for 4 or 5 days at 37° C., the number of viable cells was determined by the 3-(4,5-dimethylthiazol-2-yl)-2,5-diphenyltetrazolium bromide (MTT) method, as disclosed in *J. Virol. Methods,* 20, 309 (1988).

The cytotoxicity of the compounds of the present invention was assessed in parallel with their antiviral activity. It was based on the viability of mock-infected host cells as determined by the MTT methods (see J. Virol. Methods, 20, 309 (1988)). AZT was employed as a comparative compound.

The results of the tests are shown in Table 2.

TABLE 2

| Compound | $CD_{50}$ ($\mu$g/ml)* | $ED_{50}$ ($\mu$g/ml)** | S. I. ($CD_{50}/ED_{50}$)*** |
|---|---|---|---|
| 1 | 84.68 | <0.001 | >84,680 |
| 2 | 21.57 | <0.00256 | >8,425 |
| 3 | 16.63 | <0.001 | >16,630 |
| 4 | 92 | 0.018 | >5,111 |
| 5 | 29.66 | <0.00256 | >11,585 |
| 6 | 13.43 | <0.00256 | >5,246 |
| 7 | 10.21 | <0.001 | >10,210 |
| 8 | 9.52 | <0.00256 | >3,718 |
| 9 | 35.15 | 0.992 | 35 |
| 10 | 118.54 | 0.00351 | 33,772 |
| 11 | 128.91 | 0.01073 | 12,014 |
| 12 | 126.04 | 0.01056 | 11,933 |
| 13 | 5.86 | <0.001 | >5,860 |
| 14 | 15.33 | <0.001 | >15,330 |
| 15 | 103.46 | 0.043 | 2,406 |
| 16 | 88.72 | 0.0116 | 7,648 |
| 17 | 1.055 | <0.001 | >10,550 |
| 18 | 11.92 | <0.001 | >11,920 |
| 19 | 15.45 | <0.01 | >15,450 |
| 20 | 51.71 | 0.00367 | 14,101 |
| 21 | 121.15 | 0.0119 | 10,180 |
| AZT | 0.558 | 0.001161 | 506 |

Foot note:
*$CD_{50}$: Cytotoxic concentration that causes death of MT-4 cells by 50%
**$ED_{50}$: Effective concentration for the inhibition of the proliferation of HIV by 50%
***S. I.: Selectivity index = ($CD_{50}/ED_{50}$)

As the above results show, the novel antiviral 6-aryloxy and 6-arylcarbonyl 2,4-pyrimidinedione derivatives of the present invention possess high antiviral activity against HIV-1 and at the same time show high selectivity indices, i.e., low toxicity. The inventive compounds can therefore be used as a drug for treating AIDS.

While the invention has been described with respect to the specific embodiments, it should be recognized that various modifications and changes may be made by those skilled in the art to the invention which also fall within the scope of the invention as defined by the appended claims.

What is claimed is:

1. A compound of formula(I) and pharmaceutically acceptable salts thereof:

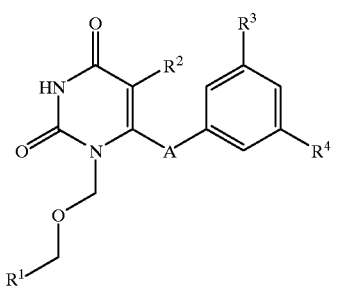

(I)

wherein:
R$^1$ is hydrogen or a $C_{1-10}$ alkyl group optionally having a substituent selected from the group consisting of aryl, $C_{1-10}$ alkoxy and $C_{2-5}$ alkylcarbonyloxy groups;

R$^2$ is hydrogen or a $C_{1-10}$ alkyl group optionally having an aryl substituent;

R$^3$ and R$^4$ are each hydrogen or a $C_{1-3}$ alkyl group; and

A is oxygen or a carbonyl group.

2. The compound of claim 1 wherein R$^1$ is methyl, acetoxymethyl or phenyl.

3. The compound of claim 2 wherein R$^2$ is ethyl or isopropyl.

4. The compound of claim 3 wherein R$^3$ and R$^4$ are each hydrogen or methyl.

5. The compound of claim 1, which is selected from the group consisting of:

1-ethoxymethyl-5-ethyl-6-(3',5'-dimethylphenoxy)-2,4-pyrimidinedione;

1-ethoxymethyl-5-isopropyl-6-(3',5'-dimethylphenoxy)-2,4-pyrimidinedione;

1-ethoxymethyl-5-ethyl-6-phenoxy-2,4-pyrimidinedione;

1-ethoxymethyl-5-isopropyl-6-phenoxy-2,4-pyrimidinedione;

1-benzyloxymethyl-5-ethyl-6-(3',5'-dimethylphenoxy)-2,4-pyrimidinedione;

1-benzyloxymethyl-5-isopropyl-6-(3',5'-dimethylphenoxy)-2,4-pyrimidinedione;

1-benzyloxymethyl-5-isopropyl-6-phenoxy-2,4-pyrimidinedione;

1-(2'-acetoxyethoxymethyl)-5-ethyl-6-(3',5'-dimethylphenoxy)-2,4-pyrimidinedione;

1-(2'-acetoxyethoxymethyl)-5-isopropyl-6-(3',5'-dimethylphenoxy)-2,4-pyrimidinedione;

1-(2'-methoxyethoxymethyl)-5-isopropyl-6-(3',5'-dimethylphenoxy)-2,4-pyrimidinedione;

1-ethoxymethyl-5-ethyl-6-(3',5'-dimethylbenzoyl)-2,4-pyrimidinedione;

1-ethoxymethyl-5-isopropyl-6-(3',5'-dimethylbenzoyl)-2,4-pyrimidinedione;

1-ethoxymethyl-5-ethyl-6-benzoyl-2,4-pyrimidinedione;

1-ethoxymethyl-5-isopropyl-6-benzoyl-2,4-pyrimidinedione;

1-benzyloxymethyl-5-ethyl-6-(3',5'-dimethylbenzoyl)-2,4-pyrimidinedione;

1-benzyloxymethyl-5-isopropyl-6-(3',5'-dimethylbenzoyl)-2,4-pyrimidinedione;

1-benzyloxymethyl-5-isopropyl-6-benzoyl-2,4-pyrimidinedione; and 1-(2'-methoxyethoxymethyl)-5-isopropyl-6-(3',5'-dimethylbenzoyl)-2,4-pyrimidinedione.

6. A process for the preparation of the compound of claim 1 which comprises silylating a compound of formula(II) to give a compound of formula(III) and coupling the compound of formula(III) with a compound of formula(IV):

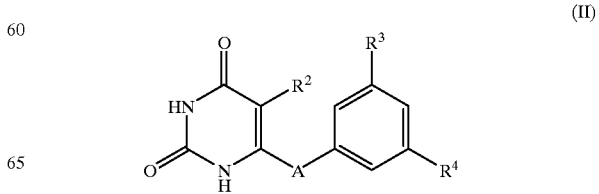

(II)

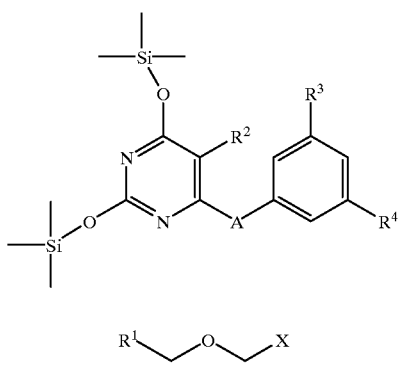

(III)

(IV)

wherein, $R^1$, $R^2$, $R^3$, $R^4$ and A have the same meanings as defined in claim 1.

7. The process of claim 6 wherein the coupling reaction is conducted using the compound of formula(III) and the compound of formula(IV) in a molar ratio of 1:0.8 to 1:1.2 in a nonpolar solvent at a temperature ranging from −20 to 100° C.

8. An antiviral composition comprising a therapeutically effective amount of the 2,4-pyrimidinedione compound or a pharmaceutically acceptable salt thereof of claim 1 as an active ingredient, and a pharmaceutically acceptable carrier and/or adjuvant.

* * * * *